United States Patent [19]
Philippe et al.

[11] Patent Number: 6,046,344
[45] Date of Patent: Apr. 4, 2000

[54] PROCESS FOR THE PREPARATION OF HYDROXYPROPYLATED QUATERNARY AMMONIUM COMPOUNDS CONTAINING AN ESTER FUNCTIONAL GROUP

[75] Inventors: Michel Philippe, Wissous; Alain Campos, Mitry Mory, both of France

[73] Assignee: L'Oreal, Paris, France

[21] Appl. No.: 08/988,216

[22] Filed: Dec. 10, 1997

[30] Foreign Application Priority Data

Dec. 11, 1996 [FR] France .................................. 96 15223

[51] Int. Cl.[7] .................................................. C07C 227/00
[52] U.S. Cl. .......................... 554/114; 554/103; 554/149
[58] Field of Search ..................... 554/114, 149, 554/103

[56] References Cited

U.S. PATENT DOCUMENTS

| | | | |
|---|---|---|---|
| 3,272,712 | 9/1966 | Kalopissis et al. | 554/110 |
| 3,329,706 | 7/1967 | Sobolev | 260/486 |
| 3,342,840 | 9/1967 | Sobolev . | |
| 3,872,138 | 3/1975 | Ogata . | |
| 4,173,539 | 11/1979 | Rule et al. . | |
| 4,840,738 | 6/1989 | Hardy et al. . | |

FOREIGN PATENT DOCUMENTS

| | | |
|---|---|---|
| 1313143 | 5/1963 | France . |
| 1793834 | 10/1976 | Germany . |

*Primary Examiner*—Deborah D. Carr
*Attorney, Agent, or Firm*—Finnegan, Henderson, Farabow, Garrett & Dunner, L.L.P.

[57] ABSTRACT

A process for the preparation of hydroxypropylated quaternary ammonium compounds containing an ester functional group, preferably a fatty acid ester functional group, of formula (I):

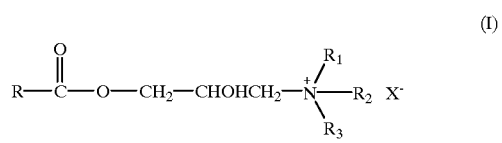

in which:

R denotes a saturated or unsaturated, linear or branched $C_7$–$C_{35}$ alkyl chain;

$R_1$, $R_2$ and $R_3$ independently denote a saturated or unsaturated, linear or branched $C_1$–$C_{18}$ alkyl chain;

$X^-$ denotes a halide or another anion chosen from:

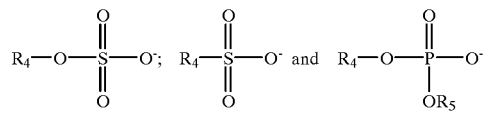

in which:

$R_4$ and $R_5$ independently denote a saturated or unsaturated, linear or branched $C_1$–$C_8$ alkyl chain, wherein the process comprises reacting, in a single step and in an alcoholic solvent at reflux, an aliphatic carboxylic acid (RCOOH) salt or an aliphatic carboxylic acid under basic catalysis conditions with a compound of formula (II):

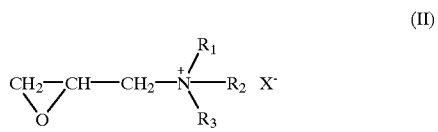

in which
$R_1$, $R_2$, $R_3$ and $X^-$ are defined as above.

15 Claims, No Drawings

PROCESS FOR THE PREPARATION OF HYDROXYPROPYLATED QUATERNARY AMMONIUM COMPOUNDS CONTAINING AN ESTER FUNCTIONAL GROUP

The present invention relates to a new process for the preparation of hydroxypropylated quaternary ammonium compounds containing an ester functional group, in particular a fatty acid ester functional group.

Certain hydroxypropylated quaternary ammonium compounds containing a fatty acid ester functional group are used in cosmetics in hair products, as treatment agents conferring sheen and a soft feel on the hair and facilitating the combing and the disentangling of the hair. These are described in French Patent No. 1,313,143 and U.S. Pat. No. 3,872,138.

According to French Patent No. 1,313,143, the disclosure of which is incorporated herein by reference, these compounds are prepared according to a two-stage synthesis process involving:

(1) reacting an alkaline salt of a fatty aliphatic carboxylic acid with an epihalohydrin, in particular epichlorohydrin, and a secondary amine in an alcoholic solvent, such as isopropanol or tert-butanol, and (2) separating the alkali metal halide formed and quaternizing the amino ester formed in the first stage with an alkylating agent, such as dimethyl sulphate.

This synthesis has the disadvantage of being lengthy and expensive and of involving epichlorohydrin, which is very toxic and problematic to employ, and requires the use of highly toxic alkylating agents.

According to U.S. Pat. No. 3,872,138, the disclosure of which is incorporated herein by reference, these same compounds can be prepared according to a two-stage process as follows:

(1) reacting a salt of a tertiary amine with a carboxylic acid in stoichiometric amounts, in order to neutralize the acid with the amine, and (2) then reacting the resulting salt with epichlorohydrin in a benzene-type solvent at a temperature of from 50 to 150° C. for a time of approximately 15 hours. This synthesis has the disadvantage of being equally lengthy and expensive and of involving epichlorohydrin and of requiring the use of very toxic solvents.

The inventors have discovered, surprisingly, a new process which makes it possible to obtain hydroxypropylated quaternary ammonium compounds containing an ester functional group, preferably a fatty acid ester functional group, in a single step, under easier, faster and safer processing conditions, without using an epihalohydrin, alkylating agents or solvents of high toxicity.

An aim of the process in accordance with the present invention is to prepare hydroxypropylated quaternary ammonium compounds containing an ester functional group, preferably a fatty acid ester functional group, and having the formula (I):

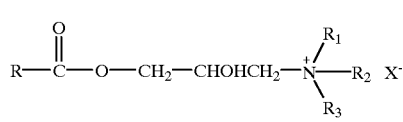

in which:

R denotes a saturated or unsaturated, linear or branched $C_7$–$C_{35}$ alkyl chain;

$R_1$, $R_2$ and $R_3$ independently denote a saturated or unsaturated, linear or branched $C_1$–$C_{18}$ alkyl chain;

$X^-$ denotes a halide (preferably chlorine) or another anion chosen from:

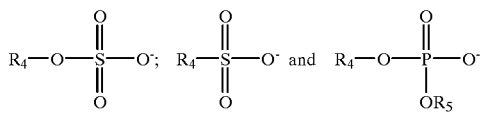

in which:

$R_4$ and $R_5$ independently denote a saturated or unsaturated, linear or branched $C_1$–$C_8$ alkyl chain.

The compounds of formula (I) where $R_1$, $R_2$ and $R_3$ simultaneously denote a methyl radical and $X^-$ denotes the chloride ion are preferably prepared.

The present process preferably involves reacting, in a single step and in an alcoholic solvent at reflux, a fatty aliphatic carboxylic acid (RCOOH) salt or a fatty aliphatic carboxylic acid under basic catalysis conditions with a compound of formula (II):

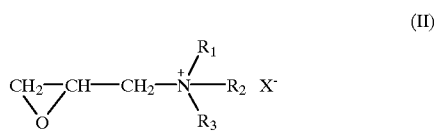

where R, $R_1$, $R_2$, $R_3$ and $X^-$ have the same meanings indicated above in formula (I).

The carboxylic acid salt is preferably an alkali metal salt, such as a sodium or potassium salt, or an alkaline-earth metal salt. Alkali metal salts are particularly preferred.

Basic catalysis is preferably achieved with sodium hydroxide, potassium hydroxide or a triethylamine.

The alcoholic solvent used is preferably chosen from lower $C_1$–$C_4$ alcohols and more particularly 2-butanol.

The reaction temperature generally ranges from 45 to 150° C. and the reaction time preferably varies from 4 to 8 hours.

According to the process of the invention, the final product obtained at the end of the reaction can subsequently be purified by simple washing and/or simple extraction based on a solvent chosen, for example, from heptane, a lower $C_1$–$C_4$ alcohol, such as methanol, or their mixtures.

The compounds of formula (I) as defined above can be used in cosmetic or dermatological compositions, in particular in hair products such as shampoos, conditioners or lotions for caring for the hair. They are used as hair treatment agents which make it possible to improve the surface condition of the individual hairs and to facilitate combing and disentangling of the hair.

The following examples serve to illustrate the invention without, however, exhibiting a limiting nature.

PREPARATION EXAMPLES

EXAMPLE 1

Preparation of [3-(2-octyldodecanoyloxy)-2-hydroxypropyl]-trimethylammonium chloride

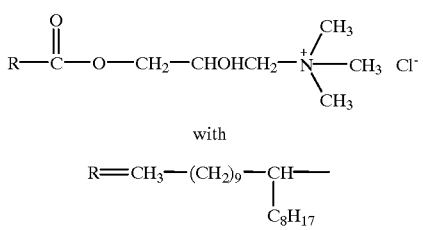

The following were introduced into a round-bottomed flask equipped with a stirrer, a thermometer, a dropping funnel and a vertical reflux condenser:

100 ml of 2-butanol,
0.15 mol of 2-octyldodecanoic acid (46.5 g), and
0.075 mol of sodium hydrogencarbonate (0.63 g).

Heating was carried out to the reflux temperature of the 2-butanol (98–99° C.). As soon as the hydrogencarbonate dissolved in the mixture, 0.15 mol (22.7 g) of glycidyltrimethylammonium chloride, dissolved in 50 ml of 2-butanol, was introduced dropwise. Refluxing was maintained for 6 hours after the end of the introduction.

The reaction mixture was washed with water and then with heptane. The upper phase was concentrated to dryness and then taken up again in a heptane/methanol/water mixture. The lower phase was concentrated to dryness. An amber-colored paste was obtained.

Analyses

Chloride number: 1.95 meq/g
Acid number: 0.43 meq/g, i.e. 19% acid (in moles)

Elemental analysis

|     | Found | Theory +19% acid +1H$_2$O |
| --- | ----- | ------------------------- |
| C   | 65.8  | 66.06                     |
| H   | 11.65 | 11.75                     |
| N   | 2.86  | 2.53                      |
| O   | 13.63 | 12.94                     |
| Cl$^-$ | 6.43 | 6.55                    |

EXAMPLE 2

Preparation of [3-(2-decyltetradecanoyloxy)-2-hydroxypropyl]-trimethylammonium chloride

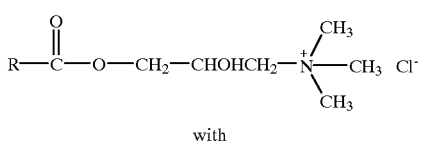

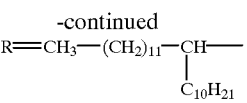

The following were introduced into a round-bottomed flask equipped with a stirrer, a thermometer, a dropping funnel and a vertical reflux condenser:

100 ml of 2-butanol,
0.15 mol of 2-decyltetradecanoic acid (36.8 g), and
0.075 mol of sodium hydrogencarbonate (0.63g).

Heating was carried out to the reflux temperature of the 2-butanol (98–99° C.). As soon as the hydrogencarbonate dissolved in the mixture, 0.15 mol (22.7 g) of glycidyltrimethylammonium chloride, dissolved in 50 ml of 2-butanol, was introduced dropwise. Refluxing was maintained for 6 hours after the end of the introduction.

The reaction mixture was washed with water and then with heptane. The upper phase was concentrated to dryness and then taken up again in a heptane/methanol/water mixture. The lower phase was concentrated to dryness. A pale-yellow paste was obtained.

Analyses

Chloride number: 1.71 meq/g
Acid number: 0.174 meq/g, i.e. 10% acid (in moles)

Elemental analysis

|     | Found | Theory +10% acid +1.5 H$_2$O |
| --- | ----- | ---------------------------- |
| C   | 66.72 | 66.6                         |
| H   | 12.06 | 12.4                         |
| N   | 2.62  | 2.4                          |
| O   | 13.35 | 12.9                         |
| Cl$^-$ | 6.03 | 6.08                       |

EXAMPLE 3

Preparation of [3-(2-butyloctanoyloxy)-2-hydroxypropyl]-trimethylammonium chloride

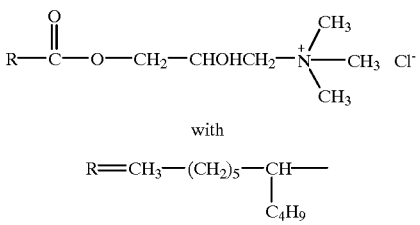

The following were introduced into a round-bottomed flask equipped with a stirrer, a thermometer, a dropping funnel and a vertical reflux condenser:

100 ml of 2-butanol,
0.15 mol of 2-butyloctanoic acid (30 g), and
0.075 mol of sodium hydrogencarbonate (0.63 g).

Heating was carried out to the reflux temperature of the 2-butanol (98–99° C.). As soon as the hydrogencarbonate dissolved in the mixture, 0.15 mol (22.7 g) of glycidyltrimethylammonium chloride, dissolved in 50 ml of 2-butanol, was introduced dropwise. Refluxing was maintained for 6 hours after the end of the introduction.

The reaction mixture was washed with water and then with heptane. The upper phase was concentrated to dryness and then taken up again in a heptane/methanol/water mixture. The lower phase was concentrated to dryness. An amber-colored paste was obtained.

Analyses

Chloride number: 2.60 meq/g

Acid number: 0.11 meq/g, i.e. 4.2% acid (in moles)

Elemental analysis

|   | Found | Theory +4.2% acid +1.5 H$_2$O |
|---|---|---|
| C | 58.5 | 57.5 |
| H | 11.03 | 10.9 |
| N | 3.83 | 3.5 |
| O | 18.54 | 18.8 |
| Cl$^-$ | 8.59 | 9.0 |

EXAMPLE 4

Preparation of [3-(2-hexyldecanoyloxy)-2-hydroxypropyl]-trimethylammonium chloride

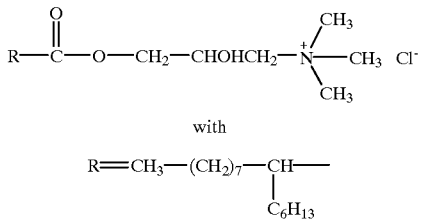

with

R=CH$_3$—(CH$_2$)$_7$—CH—
                    |
                    C$_6$H$_{13}$

The following were introduced into a round-bottomed flask equipped with a stirrer, a thermometer, a dropping funnel and a vertical reflux condenser:

100 ml of 2-butanol, 0.15 mol of 2-hexyldecanoic acid (38.4 g), and 0.075 mol of sodium hydrogencarbonate (0.63 g).

Heating was carried out to the reflux temperature of the 2-butanol (98–99° C.). As soon as the hydrogencarbonate dissolved in the mixture, 0.15 mol (22.7 g) of glycidyltrimethylammonium chloride, dissolved in 50 ml of 2-butanol, was introduced dropwise. Refluxing was maintained for 6 hours after the end of the introduction.

The reaction mixture was washed with water and then with heptane. The upper phase was concentrated to dryness and then taken up again in a heptane/methanol/water mixture. The lower phase was concentrated to dryness. An amber-colored paste was obtained.

Analyses

Chloride number: 1.98 meq/g

Acid number: 0.066 meq/g, i.e. 3.3% acid (in moles)

Elemental analysis

|   | Found | Theory +3.3% acid +15 H$_2$O |
|---|---|---|
| C | 56.1 | 56.6 |
| H | 11.15 | 11.21 |
| N | 3.5 | 2.93 |
| O | 22.1 | 21.6 |
| Cl$^-$ | 6.91 | 7.44 |

We claim:

1. A process for preparing a hydroxypropylated quaternary ammonium compound of the formula (I):

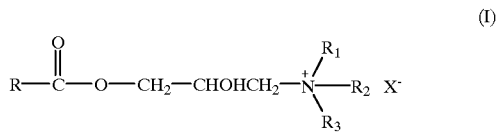

in which:

R denotes a saturated or unsaturated, linear or branched C$_7$–C$_{35}$ alkyl chain;

R$_1$, R$_2$ and R$_3$ independently denote a saturated or unsaturated, linear or branched C$_1$–C$_{18}$ alkyl chain;

X$^-$ denotes a halide or another anion, said anion being:

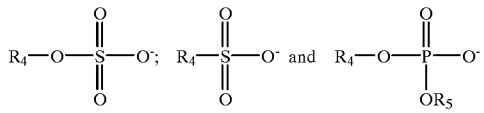

in which:

R$_4$ and R$_5$ independently denote a saturated or unsaturated, linear or branched C$_1$–C$_8$ alkyl chain, said process comprising reacting, in a single step and in an alcoholic solvent at reflux, an aliphatic carboxylic acid (RCOOH) salt or an aliphatic carboxylic acid under basic catalysis conditions with a compound of formula (bi):

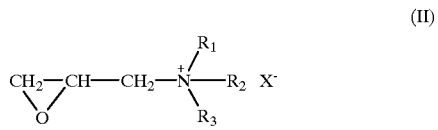

in which

R denotes a saturated or unsaturated, linear or branched C$_7$–C$_{35}$ alkyl chain;

R$_1$, R$_2$ and R$_3$ independently denote a saturated or unsaturated, linear or branched C$_1$–C$_{18}$ alkyl chain; and X⁻ denotes a halide or another anion, said anion being:

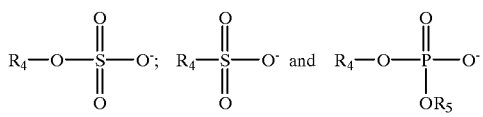

in which:
R₄ and R₅ independently denote a saturated or unsaturated, linear or branched $C_1$–$C_8$ alkyl chain.

2. A process according to claim 1, wherein $R_1$, $R_2$ and $R_3$ simultaneously denote methyl and X⁻ denotes the chloride ion.

3. A process according to claim 1, wherein said fatty aliphatic carboxylic acid (RCOOH) salt is an alkali metal salt or an alkaline-earth metal salt.

4. A process according to claim 3, wherein said fatty aliphatic carboxylic acid (RCOOH) salt is an alkali metal salt.

5. A process according to claim 4, wherein said alkali metal salt is a sodium salt or a potassium salt.

6. A process according to claim 1, wherein said alcoholic solvent is a lower $C_1$–$C_4$ alcohol.

7. A process according to claim 6, wherein said alcoholic solvent is 2-butanol.

8. A process according to claim 1, wherein said reaction occurs at a temperature ranging from 45 to 150° C. and for a time ranging from 4 to 8 hours.

9. A process according to claim 1, further comprising purifying the product of said reaction, by washing or extracting with at least one solvent.

10. A process according to claim 9, wherein said at least one solvent is heptane or a lower $C_1$–$C_4$ alcohol.

11. A process according to claim 1, wherein said basic catalysis conditions include the presence of sodium hydroxide, potassium hydroxide or a triethylamine.

12. A process according to claim 11, wherein said basic catalysis involves a triethylamine.

13. A process according to claim 12, wherein said triethylamine is glycidyltrimethylammonium chloride.

14. A process according to claim 9, wherein said purifying is achieved by washing or extracting with methanol.

15. A process according to claim 1, wherein said aliphatic carboxylic acid salt or said aliphatic carboxylic acid is a fatty aliphatic carboxylic acid salt or a fatty aliphatic carboxylic acid.

* * * * *

UNITED STATES PATENT AND TRADEMARK OFFICE
CERTIFICATE OF CORRECTION

PATENT NO. : 6,046,344
DATED : April 4, 2000
INVENTOR(S) : PHILIPPE, et al.

It is certified that error appears in the above-indentified patent and that said Letters Patent is hereby corrected as shown below:

In claim 1 , column 6, line 39, "and" should read --or--; line 53, "(bi)" should read --II--; column 7, line 5, "and" should read --or--.

Signed and Sealed this

Twenty-seventh Day of March, 2001

Attest:

NICHOLAS P. GODICI

Attesting Officer

Acting Director of the United States Patent and Trademark Office